United States Patent
Liu et al.

(10) Patent No.: US 10,040,862 B2
(45) Date of Patent: Aug. 7, 2018

(54) HUMANIZED AND CHIMERIC MONOCLONAL ANTIBODIES TO CD99

(71) Applicant: The Board of Trustees of the Leland Stanford Junior University, Stanford, CA (US)

(72) Inventors: Jie Liu, Palo Alto, CA (US); Ronald Levy, Stanford, CA (US); Ravindra Majeti, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 15/303,720

(22) PCT Filed: Apr. 17, 2015

(86) PCT No.: PCT/US2015/026491
§ 371 (c)(1),
(2) Date: Oct. 12, 2016

(87) PCT Pub. No.: WO2015/161267
PCT Pub. Date: Oct. 22, 2015

(65) Prior Publication Data
US 2017/0029524 A1    Feb. 2, 2017

Related U.S. Application Data

(60) Provisional application No. 61/981,681, filed on Apr. 18, 2014.

(51) Int. Cl.
*A61K 39/00* (2006.01)
*C07K 16/28* (2006.01)
*A61K 39/395* (2006.01)

(52) U.S. Cl.
CPC ...... *C07K 16/2896* (2013.01); *C07K 16/2803* (2013.01); *A61K 39/39558* (2013.01); *A61K 2039/505* (2013.01); *A61K 2039/507* (2013.01); *C07K 2317/24* (2013.01); *C07K 2317/565* (2013.01); *C07K 2317/73* (2013.01); *C07K 2317/732* (2013.01); *C07K 2317/92* (2013.01)

(58) Field of Classification Search
CPC .................. A61K 2039/505; A61K 39/39558
See application file for complete search history.

(56) References Cited

U.S. PATENT DOCUMENTS

| | | |
|---|---|---|
| 6,451,578 B1 | 9/2002 | Simons et al. |
| 7,214,786 B2 | 5/2007 | Kovalic et al. |
| 8,722,043 B2 | 5/2014 | Borg et al. |
| 2010/0297664 A1 | 11/2010 | Wadhwa et al. |
| 2011/0217292 A1 | 9/2011 | Newman et al. |
| 2012/0004117 A1 | 1/2012 | Aburatani et al. |
| 2012/0282257 A1 | 11/2012 | Picci et al. |

FOREIGN PATENT DOCUMENTS

| | | |
|---|---|---|
| WO | 2005025618 A2 | 4/2005 |
| WO | 2016022971 A1 | 2/2016 |

OTHER PUBLICATIONS

Rudikoff et al. (Proc. Natl. Acad. Sci. USA. 1982; 79: 1979-1983).*
Mariuzza et al. (Annu. Rev. Biophys. Biophys. Chem. 1987; 16: 139-159).*
Gussow et al. (Methods in Enzymology. 1991; 203: 99-121).*
Winkler et al. (J. Immunol. Oct. 15, 2000; 165 (8): 4505-4514).*
Giusti et al. (Proc. Natl. Acad. Sci. USA. May 1987; 84 (9): 2926-2930).*
Chien et al. (Proc. Natl. Acad. Sci. USA. Jul. 1989; 86 (14): 5532-5536).*
Caldas et al. (Mol. Immunol. May 2003; 39 (15): 941-952).*
Vajdos et al. (J. Mol. Biol. Jul. 5, 2002; 320 (2): 415-428).*
De Pascalis et al. (J. Immunol. 2002; 169 (6): 3076-3084).*
Wu et al. (J. Mol. Biol. Nov. 19, 1999; 294 (1): 151-162).*
Casset et al. (Biochem. Biophys. Res. Commun. Jul. 18, 2003; 307 (1): 198-205).*
MacCallum et al. (J. Mol. Biol. Oct. 11, 1996; 262 (5): 732-745).*
Holm et al. (Mol. Immunol. Feb. 2007; 44 (6): 1075-1084).*
Yu et al. (PLoS One. 2012; 7 (3): e33340; pp. 1-15).*
Chang et al. (Structure. Jan. 7, 2014; 22 (1): 9-21).*
Gura (Science. 1997; 278: 1041-1042).*
Dennis (Nature. Aug. 7, 2006; 442: 739-741).*
Saijo et al. (Cancer Sci. Oct. 2004; 95 (10): 772-776).*
Kelland (Eur. J. Cancer. Apr. 2004; 40 (6): 827-836).*
Peterson et al. (Eur. J. Cancer. 2004; 40: 837-844).*
Bergers et al. (Current Opinion in Genetics and Development. 2000; 10: 120-127).*
Husak et al. "CD99 Ligation Upregulates HSP70 On Acute Lymphoblastic Leukemia Cells And Concomitantly Increases NK Cytotoxicity", Cell Death and Disease, Nov. 15, 2012, pp. 1-6, Nature Publishing Group, London, United Kingdom.
GenBank Database, Accession BCM16203, "Anti-CD20 antibody light chain-SIRP alpha fusion construct, SEQ ID13." Apr. 21, 2016.
Levy et al., "A human thymus-leukemia antigen defined by hybridoma monoclonal antibodies", Proceedings National Academy of Sciences, Dec. 1, 1979, pp. 6552-6556, vol. 76, No. 12,1, Washington, DC.

(Continued)

*Primary Examiner* — Stephen Rawlings
(74) *Attorney, Agent, or Firm* — Pamela J. Sherwood; Bozicevic, Field & Francis LLP

(57) ABSTRACT

Humanized or chimeric anti-CD99 monoclonal antibodies are provided. The antibodies bind to and neutralize human CD99, and find use in various therapeutic methods. Embodiments of the invention include isolated antibodies and derivatives and fragments thereof, pharmaceutical formulations comprising one or more of the humanized or chimeric anti-CD99 monoclonal antibodies; and cell lines that produce these monoclonal antibodies. Also provided are amino acid sequences of the antibodies.

11 Claims, 8 Drawing Sheets
(3 of 8 Drawing Sheet(s) Filed in Color)

(56) References Cited

OTHER PUBLICATIONS

"Monoclonal Mouse Anti-Human CD99, Ewing's Sarcoma Marker MIC2 Gene Product Clone 12E7" DAKO, Mar. 2007, pp. 1-2, https://www.dako.it/prod_downloadpackageinsert.pdf?objectid=109776002.

* cited by examiner

FIG. 1A

EVQLQQSGAELVKPGASVKLSCTASGFNIK
       <u>CDR1</u>                    <u>CDR2</u>
DTYIHWVKRRPEQGLEWIGRIDPANGNTK
<u>       </u>
YDPKFQGKATITADTSSNTAYLQLSSLTSED
                <u>CDR3</u>
TAVYYCARRGGVDWGQGTLVTVSA

FIG. 1B
                                       <u>  CDR1  </u>
DVVMTQTPLTLSVTIGQPASISCKSSQSLLD
<u>              </u>              <u>  CDR2  </u>
GDGKTYLNWLLQRPGQSPKRLIYLVSKLDS

GVPDRFTGSGSGTDFTLKISRVEAEDLGVY
      <u>   CDR3    </u>
YCWQGTHFPRTFGGGTKLEIK

FIG. 2A

```
                                                           CDR1
                                                     ─────────────
12E7-VH      EVQLQQSGAELVKPGASVKLSCTASGFNIKDTYIH
Hu12E7-VH    QVQLVQSGAEVKKPGASVKVSCKASGYTFKDTYIH
                                          CDR2
                                 ─────────────────────────
12E7-VH      WVKRPEQGLEWIGRIDPANGNTKYDPKFQGKATI
Hu12E7-VH    WVRQAPGQGLEWMGRIDPANGNTKYDPKFQGRVTM
                                                      CDR3
                                                    ───────
12E7-VH      TADTSSNTAYLQLSSLTSEDTAVYYCARRGGVDWG
Hu12E7-VH    TRDTSISTAYMELSRLRSDDTAVYYCARRGGVDWG

12E7-VH      QGTLVTVSA
Hu12E7-VH    QGTLVTVSS
```

FIG. 2B

```
                                                       CDR1
                                                   ─────────────
12E7-VL      DVVMTQTPLTLSVTIGQPASISCKSSQSLLD
Hu12E7-VL !! DIVMTQTPLSLSVTPGQPASISCKSSQSLLD             !
                                         CDR2
                              ─────────────────────────
12E7-VL      GDGKTYLNWLLQRPGQSPKRLIYLVSKLDSGV
Hu12E7-VL    GDGKTYLNWLLQKPGQSPQRLIYLVSKLDSGV!
                                                CDR3
                                               ─────
12E7-VL      PDRFTGSGSGTDFTLKISRVEAEDLGVYYCWQ
Hu12E7-VL    PDRFSGSGSGTDFTLKISRVEAEDVGVYYCWQ!           !

─────────
12E7-VL      GTHFPRTFGGGTKLEIK
Hu12E7-VL    GTHFPRTFGQGTKLEIK
!
```

QVQLVQSGAEVKKPGASVKVSCKASGFNIKDTYIHWVRQAPGQGLEWMGRIDPANGNTKY
DPKFQGRVTMTRDTSISTAYMELSRLRSDDTAVYYCARRGGVDWGQGTLVTVSS

HUMANIZED AND CHIMERIC MONOCLONAL ANTIBODIES TO CD99

CROSS REFERENCE

This application claims benefit and is a 371 application of PCT Application No. PCT/US2015/026491, filed Apr. 17, 2015, which claims benefit of U.S. Provisional Patent Application No. 61/981,681, filed Apr. 18, 2014, which applications are incorporated herein by reference in their entirety.

BACKGROUND OF THE INVENTION

CD99 antigen (Cluster of differentiation 99) also known as MIC2 or single-chain type-1 glycoprotein is a heavily O-glycosylated transmembrane protein that is encoded by the CD99 gene in humans. CD99 has a key role in several biological processes, including cell adhesion, migration, and apoptosis; differentiation of T cells and thymocytes; diapedesis of lymphocytes to inflamed vascular endothelium; maintenance of cellular morphology; and regulation of intracellular membrane protein trafficking.

CD99 was originally described as a human thymus-leukemia antigen and found to be expressed brightly on cortical thymocytes and T-lineage acute lymphoblastic leukemia (T-ALL), whereas normal peripheral blood lymphocytes appeared to exhibit only low expression levels. It has been reported and used as a marker for detection of minimal residual disease (MRD) in T-ALL. In addition, CD99 is found on the cell surface of Ewing's sarcoma tumors (EWS) and is positive in granulosa cell tumors. Cell surface expression of CD99 is a very consistent feature of EWS, and indeed, CD99 is currently considered to be one of the best diagnostic immunohistochemical markers for this disease. When CD99 expression is knocked down in human Ewing's sarcoma cells, and those cells are grafted onto mice, development of tumors and bone metastasis is reduced.

CD99 expression on acute myeloid leukemia stem cells (AML LSC) compared to normal hematopoietic stem cell (HSC) has been compared and shown to be increased 5.6 fold in AML LSC compared to HSC, suggesting that CD99 can serve as an AMLSC marker in tumor targeting.

The present invention provides anti-CD99 antibodies having low immunogenicity in humans.

SUMMARY OF THE INVENTION

Compositions and methods are provided relating to humanized or chimeric anti-CD99 monoclonal antibodies. The antibodies of the invention bind to human CD99, and find use in various therapeutic methods. Embodiments of the invention include isolated antibodies and derivatives and fragments thereof, pharmaceutical formulations comprising one or more of the humanized or chimeric anti-CD99 monoclonal antibodies; and cell lines that produce these monoclonal antibodies. Also provided are amino acid sequences of the antibodies.

Antibodies of interest include the provided humanized or chimeric antibodies, and variants thereof. The monoclonal antibodies of the invention find particular utility as reagents for the diagnosis and immunotherapy of disease associated with CD99 in humans, particularly in cancer therapy. An advantage of the monoclonal antibodies of the invention derives from the humanization process. Thus, in vivo use of the monoclonal antibodies of the invention for immunotherapy greatly reduces the problems of significant host immune response to the antibodies.

Various forms of the antibodies are contemplated herein. For example, the anti-CD99 antibody may be a full length chimeric or humanized antibody, e.g. having a human immunoglobulin constant region of any isotype, e.g. IgG1, IgG2, IgG3, IgG4, IgA, etc. or an antibody fragment, e.g. a F(ab')$_2$ fragment, and F(ab) fragment, etc. Fragments comprising CDR regions are also of interest, e.g. for imaging purposes. Furthermore, the antibody may be labeled with a detectable label, immobilized on a solid phase and/or conjugated with a heterologous compound. The antibody may also be provided as a bi-specific or multispecific antibody reactive with a second antigen, particularly including other cancer antigens; or with immunotherapy reagents, e.g. CTLA-4, CD40, CD47, and the like.

Diagnostic and therapeutic uses for the antibody are contemplated, particularly relating to the detection and elimination of undesirable cells expressing CD99. In one diagnostic application, the invention provides a method for determining the presence of CD99 expressing cancer cells, comprising exposing a patient sample suspected of containing CD99 expressing cancer cells to the anti-CD99 antibody and determining binding of the antibody to the sample. For this use, the invention provides a kit comprising the antibody and instructions for using the antibody.

The antibodies of the invention are particularly efficacious in the treatment of disease, e.g. killing cancer cells by ADCC or other mechanisms, increasing the phagocytosis of CD99 expressing cells by a combination therapy with an anti-CD47 reagent; and the like. Treatment may be systemic or localized, e.g. delivery by intratumoral injection, etc.

Embodiments of the invention include isolated antibodies and derivatives and fragments thereof that comprise at least one, usually at least 3 CDR sequences as provided herein, usually in combination with framework sequences from a human variable region or as an isolated CDR peptide. In some embodiments an antibody comprises at least one light chain comprising the 3 light chain CDR sequences provided herein situated in a variable region framework, which may be, without limitation, a human or mouse variable region framework, and at least one heavy chain comprising the 3 heavy chain CDR sequence provided herein situated in a variable region framework, which may be, without limitation, a human or mouse variable region framework.

In other embodiments, the antibody comprises an amino acid sequence variant of one or more of the CDRs of the provided antibodies, which variant comprises one or more amino acid insertion(s) within or adjacent to a CDR residue and/or deletion(s) within or adjacent to a CDR residue and/or substitution(s) of CDR residue(s) (with substitution(s) being the preferred type of amino acid alteration for generating such variants). Such variants will normally have a binding affinity for human CD99 of at least about $10^{-8}$ M and will bind to the same epitope as an antibody having the amino acid sequence of those set forth herein. Various forms of the antibodies are contemplated herein. For example, the antibody may be a full length antibody, e.g. having a human immunoglobulin constant region of any isotype, e.g. IgG1, IgG2, IgG3, IgG4, IgA, etc. or an antibody fragment, e.g. a F(ab')$_2$ fragment, and F(ab) fragment, etc. Furthermore, the antibody may be labeled with a detectable label, immobilized on a solid phase and/or conjugated with a heterologous compound.

The invention further provides: isolated nucleic acid encoding the antibodies and variants thereof; a vector comprising that nucleic acid, optionally operably linked to control sequences recognized by a host cell transformed with the vector; a host cell comprising that vector; a process for producing the antibody comprising culturing the host cell so that the nucleic acid is expressed and, optionally, recovering the antibody from the host cell culture (e.g. from the host cell culture medium). The invention also provides a composition comprising one or more of the humanized anti-CD99 antibodies and a pharmaceutically acceptable carrier or diluent. This composition for therapeutic use is sterile and may be lyophilized, e.g. being provided as a pre-pack in a unit dose with diluent and delivery device, e.g. inhaler, syringe, etc.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1A-1B. Amino acid sequence SEQ ID NO:1 of variable heavy (FIG. 1A) and SEQ ID NO:3 light (FIG. 1B) regions. CDRs are marked as indicated.

FIG. 2A-2B. Comparison of mouse and humanized 12E7 variable heavy (FIG. 2A), SEQ ID NO:1 and SEQ ID NO:2; and light (FIG. 2B) regions SEQ ID NO:3 and SEQ ID NO:4. CDRs are marked as indicated.

(FIG. 3A) Humanized 12E7 binds human CD99 with similar affinity and dose response compared to chimeric 12E7 sharing variable domains with the parental antibody. Human CD99/Fc fusion protein was coated in a 96-well plate and different concentrations of the indicated antibodies were added. HRP-conjugated anti-human Kappa antibody was used as a secondary antibody. (FIG. 3B) Hu12E7-G1 competed with the original mouse 12E7 for human CD99 binding. Human CD99/Fc fusion protein was coated in a 96-well plate and 0.5 µg of mouse 12E7 was added to the plate in the absence or presence of 1×-, 10×-, 50×-, or 100×-fold more Hu12E7-G1. HRP-conjugated anti-mouse kappa antibody was used as a secondary antibody to detect binding of mouse 12E7 to CD99.

(FIG. 7A) Primary human AML cells from three independent cases were transplanted into immunodeficient NSG mice. (FIG. 7A(i)) 12 weeks later, engraftment of AML was assessed in the peripheral blood and mice were assigned to treatment with control mouse IgG, mouse anti-human CD99 (m12E7) antibody, or a chimeric 12E7-IgG1 antibody. Mice were treated with 14 days of antibody with daily 100 µg doses, at the end of which the peripheral blood was reassessed for leukemic cells. *p<0.001. (FIG. 7B) Primary human AML cells from one case were transplanted into immunodeficient NSG mice. (FIG. 7A(i)) 10 weeks later, engraftment of AML was assessed in the peripheral blood and mice were assigned to treatment with control mouse IgG, chimeric 12E7-IgG1, chimeric 12E7-IgG4 antibody, or humanized 12E7-IgG1. Mice were treated with 14 days of antibody with daily 100 µg doses, at the end of which the peripheral blood was reassessed for leukemic cells. *p<0.05. (FIG. 7C) Primary human AML cells from two independent cases were transplanted into immunodeficient NSG mice. (FIG. 7C(i)) 10 weeks later, engraftment of AML was assessed in the bone marrow and mice were assigned to treatment with control mouse IgG or Hu12E7-G1. Mice were treated with 14 days of antibody with daily 200 µg doses. At the end of the 14 days, the bone marrow was reassessed for leukemic engraftment by flow cytometry. *p<0.001.

(FIG. 8) Anti-Human CD99 Monoclonal Antibody Synergizes with Anti-Human CD47 to Eliminate Primary Human AML Cells In Vivo. Primary human AML cells from two independent cases were transplanted into immunodeficient NSG mice. (FIG. 8(i)) 10 weeks later, engraftment of AML was assessed in the bone marrow and mice were assigned to treatment with control mouse IgG, mouse anti-human CD99 (m12E7) antibody, anti-human CD47 (Hu5F9-G4), or a combination of m12E7 and Hu5F9-G4. Mice were treated with 14 days of antibody with daily 200 µg doses for m12E7 or 10 µg doses for Hu5F9-G4. At the end of the 14 days, the bone marrow was reassessed for leukemic engraftment by flow cytometry. *p<0.02 for both comparisons.

DETAILED DESCRIPTION OF THE INVENTION

Figure 3A:
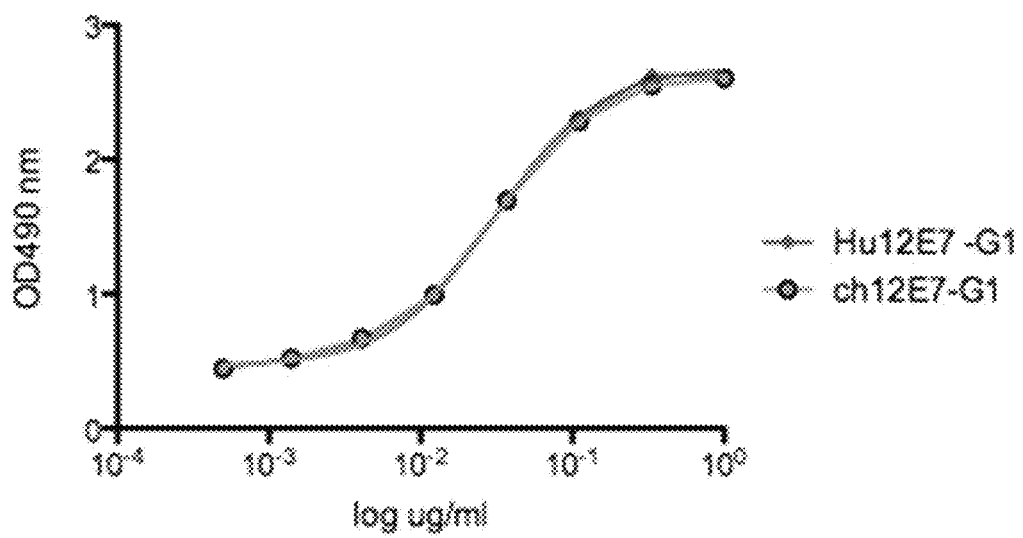
FIG. 3A-3B.

The present invention relates to humanized monoclonal antibodies which are specific for CD99. Also disclosed is a nucleic acid, and amino acid sequence of such antibodies. The antibodies find use in therapeutic and diagnostic methods associated with CD99.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity. "Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity.

Polypeptides of the latter kind are, for example, produced at low levels by the lymph system and at increased levels by myelomas.

As used in this invention, the term "epitope" means any antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

"Native antibodies and immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light- and heavy-chain variable domains (Clothia et al., J. Mol. Biol. 186:651 (1985); Novotny and Haber, Proc. Natl. Acad. Sci. U.S.A. 82:4592 (1985)).

The antibodies suitable for practicing the methods of the present invention may be bispecific, trispecific or of greater multispecificity. Bispecific antibodies comprise one binding site for CD99 according to the compositions described herein, and a binding site for SIRPα, CD47, additional cancer cell markers, and the like. Further, the antibodies of the present invention may have low risk of toxicity against granulocyte (neutrophil), NK cells, and $CD4^+$ cells as bystander cells.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Similar procedures are disclosed in WO 93/08829, and in Traunecker et al, EMBO J., 10:3655-3659 (1991). According to another approach described in WO96/27011, the interface between a pair of antibody molecules can be engineered to maximize the percentage of heterodimers which are recovered from recombinant cell culture. Such interfaces may comprise at least a part of the $CH_3$ domain of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers. An alternative method links two different single chain variable regions to heat stable antigen (HSA). Using HSA as linker increases serum half life, and has the benefit of low immunogenicity.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kos-telny et al., J. Immunol, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994). Alternatively, the antibodies can be "linear antibodies" as described in Zapata et al. Protein Eng. 8(10): 1057-1062 (1995). Briefly, these antibodies comprise a pair of tandem Fd segments ($V_H$-$C_{H1}$-$V_H$-$C_{H1}$) which form a pair of antigen binding regions. Linear antibodies can be bispecific or monospecific.

Within the context of the present invention, antibodies are understood to include monoclonal antibodies and polyclonal antibodies, antibody fragments (e.g., Fab and F(ab')$_2$), chimeric antibodies bifunctional or bispecific antibodies and tetrameric antibody complexes. Antibodies are understood to be reactive against a selected antigen if they bind with an appropriate affinity (association constant), e.g. greater than or equal to $10^7 M^{-1}$. Additionally, antibodies that may be used in the methods of the present invention may also be described or specified in terms of their binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-9}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, $10^{-15}$ M.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from the other chain, contribute to the formation of the antigen-binding site of antibodies (see Kabat et al., Sequences of Proteins of Immunological Interest, Fifth Edition, National Institute of Health, Bethesda, Md. (1991)). The constant domains are not involved directly in binding an antibody to an antigen, but exhibit various effector functions, such as participation of the antibody in antibody-dependent cellular toxicity.

The variable region sequences of exemplary anti-CD99 heavy and light chains combinations are set forth in the sequence listing, including 12E7: SEQ ID NO:1-5, where SEQ ID NO:1, 2 and 5 are VH sequences and SEQ ID NO:3-4 are VL sequences. In some embodiments the variable sequences for a particularly heavy and light chain combination as set forth in 12E7 will be maintained in a combination, i.e. a humanized antibody will comprise both 12E7 heavy chain CDR sequences and 12E7 light chain CDR sequences.

A VH sequence of the invention may contain any of the provided VH sequences, e.g. SEQ ID NO:1, 2 or 5; or may comprise the VH CDR sequences of the invention, SEQ ID NO:6, 7 and 8, in the framework of a human VH sequence. Specifically the 12E7 heavy chain CDR sequences are: SEQ ID NO:6, DTYIH (CDR1); SEQ ID NO:7, RIDPANGNT-KYDPKFQG (CDR2); SEQ ID NO:8, RGGVD (CDR3).

A VL sequence of the invention may contain any of the provided VL sequences, e.g. SEQ ID NO:3 or 4; or may comprise the VL CDR sequences of the invention, SEQ ID NO:9, 10 and 11, in the framework of a human VL sequence. The 12E7 light chain CDR sequences are SEQ ID NO:9, KSSQSLLDGDGKTYLN (CDR1); SEQ ID NO:10, LVSKLDS (CDR2); SEQ ID NO:11, WQGTHFPRT (CDR3).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. In a two-chain Fv species, this region consists of a dimer of one heavy- and one light-chain variable domain in tight, non-covalent association. In a single-chain Fv species (scFv), one heavy- and one light-chain variable domain can be covalently linked by a flexible peptide linker such that the light and heavy chains can associate in a "dimeric" structure analogous to that in a two-chain Fv species. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site. For a review of scFv see Pluckthun, in The Pharmacology of Monoclonal Antibodies, vol. 113, Rosenburg and Moore eds., Springer-Verlag, New York, pp. 269-315 (1994).

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

There are five major classes of immunoglobulins: IgA, IgD, IgE, IgG, and IgM, and several of these can be further divided into subclasses (isotypes), e.g., IgG$_1$, IgG$_2$, IgG$_3$, IgG$_4$, IgA$_1$, IgA$_2$. The heavy-chain constant domains that correspond to the different classes of immunoglobulins are called α, δ, ε, γ, and μ respectively. The subunit structures and three-dimensional configurations of different classes of immunoglobulins are well known.

"Antibody fragment", and all grammatical variants thereof, as used herein are defined as a portion of an intact antibody comprising the antigen binding site or variable region of the intact antibody, wherein the portion is free of the constant heavy chain domains (i.e. CH2, CH3, and CH4, depending on antibody isotype) of the Fc region of the intact antibody. Examples of antibody fragments include Fab, Fab', Fab'-SH, F(ab')$_2$, and Fv fragments; diabodies; any antibody fragment that is a polypeptide having a primary structure consisting of one uninterrupted sequence of contiguous amino acid residues (referred to herein as a "single-chain antibody fragment" or "single chain polypeptide"), including without limitation (1) single-chain Fv (scFv) molecules (2) single chain polypeptides containing only one light chain variable domain, or a fragment thereof that contains the three CDRs of the light chain variable domain, without an associated heavy chain moiety and (3) single chain polypeptides containing only one heavy chain variable region, or a fragment thereof containing the three CDRs of the heavy chain variable region, without an associated light chain moiety; and multispecific or multivalent structures formed from antibody fragments. In an antibody fragment comprising one or more heavy chains, the heavy chain(s) can contain any constant domain sequence (e.g. CH1 in the IgG isotype) found in a non-Fc region of an intact antibody, and/or can contain any hinge region sequence found in an intact antibody, and/or can contain a leucine zipper sequence fused to or situated in the hinge region sequence or the constant domain sequence of the heavy chain(s).

Unless specifically indicated to the contrary, the term "conjugate" as described and claimed herein is defined as a heterogeneous molecule formed by the covalent attachment of one or more antibody fragment(s) to one or more polymer molecule(s), wherein the heterogeneous molecule is water soluble, i.e. soluble in physiological fluids such as blood, and wherein the heterogeneous molecule is free of any structured aggregate. A conjugate of interest is PEG. In the context of the foregoing definition, the term "structured aggregate" refers to (1) any aggregate of molecules in aqueous solution having a spheroid or spheroid shell structure, such that the heterogeneous molecule is not in a micelle or other emulsion structure, and is not anchored to a lipid bilayer, vesicle or liposome; and (2) any aggregate of molecules in solid or insolubilized form, such as a chromatography bead matrix, that does not release the heterogeneous molecule into solution upon contact with an aqueous phase. Accordingly, the term "conjugate" as defined herein encompasses the aforementioned heterogeneous molecule in a precipitate, sediment, bioerodible matrix or other solid capable of releasing the heterogeneous molecule into aqueous solution upon hydration of the solid.

The term "monoclonal antibody" (mAb) as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Each mAb is directed against a single determinant on the antigen. In addition to their specificity, the monoclonal antibodies are advantageous in that they can be synthesized by hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made in an immortalized B cell or hybridoma thereof, or may be made by recombinant DNA methods.

The monoclonal antibodies herein include hybrid and recombinant antibodies produced by splicing a variable (including hypervariable) domain of an anti-CD99 antibody with a constant domain of another species (e.g. "humanized" antibodies), or a light chain with a heavy chain, or a chain from one species with a chain from another species, or fusions with heterologous proteins, regardless of species of origin or immunoglobulin class or subclass designation, as well as antibody fragments (e.g., Fab, F(ab')$_2$, and Fv), so long as they exhibit the desired biological activity. Of particular interest are the CDR regions of 12E7 defined herein, spliced into a human variable chain framework sequence.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In some embodiments, the antibody will be purified (1) to greater than 75% by weight of antibody as determined by the Lowry method, and most preferably more than 80%, 90% or 99% by weight, or (2) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

The term "epitope tagged" when used herein refers to an anti-CD99 antibody fused to an "epitope tag". The epitope tag polypeptide has enough residues to provide an epitope against which an antibody can be made, yet is short enough such that it does not interfere with activity of the CD99 antibody. The epitope tag preferably is sufficiently unique so that the antibody specific for the epitope does not substantially cross-react with other epitopes. Suitable tag polypeptides generally have at least 6 amino acid residues and usually between about 8-50 amino acid residues (preferably between about 9-30 residues). Examples include the c-myc tag and the 8F9, 3C7, 6E10, G4, B7 and 9E10 antibodies thereto (Evan et al., Mol. Cell. Biol. 5(12):3610-3616 (1985)); and the Herpes Simplex virus glycoprotein D (gD) tag and its antibody (Paborsky et al., Protein Engineering 3(6):547-553 (1990)).

The word "label" when used herein refers to a detectable compound or composition which is conjugated directly or indirectly to the antibody. The label may itself be detectable by itself (e.g., radioisotope labels or fluorescent labels) or, in the case of an enzymatic label, may catalyze chemical alteration of a substrate compound or composition which is detectable.

By "solid phase" is meant a non-aqueous matrix to which the antibody of the present invention can adhere. Examples of solid phases encompassed herein include those formed partially or entirely of glass (e.g. controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g. an affinity chromatography column). This term also includes a discontinuous solid phase of discrete particles, such as those described in U.S. Pat. No. 4,275,149.

Polypeptides

In one aspect, the present invention is directed to humanized or chimeric monoclonal antibodies that are specifically bind to CD99, and cell lines that produce such antibodies. Variable regions of exemplary antibodies are provided. Antibodies of interest include these provided combinations, as well as fusions of the variable regions to appropriate constant regions or fragments of constant regions, e.g. to generate F(ab)' antibodies. Variable regions of interest include at least one CDR sequence of the provided anti-CD99 antibody, where a CDR may be 3, 4, 5, 6, 7, 8, 9, 10, 11, 12 or more amino acids. Usually variable regions of interest include a "set" of CDR sequences, i.e. SEQ ID NO:6, 7 and 8 in a variable region; and/or SEQ ID NO:9, 10 and 11 in a variable region, where the two can be paired. Alternatively, antibodies of interest include a variable region as set forth in the provided antibodies, or pairs of variable regions sequences as set forth herein.

In some embodiments a polypeptide of interest has a contiguous sequence of at least about 10 amino acids, at least about 15 amino acids, at least about 20 amino acids, at least about 25 amino acids, at least about 30 amino acids, up to the complete provided variable region. Polypeptides of interest also include variable regions sequences that differ by up to one, up to two, up to 3, up to 4, up to 5, up to 6 or more amino acids as compared to the amino acids sequence set forth herein. In other embodiments a polypeptide of interest is at least about 80%, at least about 85%, at least about 90%, at least about 95%, at least about 99% identical to the amino acid sequence set forth herein.

In addition to Fabs, smaller antibody fragments and epitope-binding peptides having binding specificity for at least one epitope of CD99 are also contemplated by the present invention and can also be used in the methods of the invention. For example, single chain antibodies can be constructed according to the method of U.S. Pat. No. 4,946,778 to Ladner et al, which is incorporated herein by reference in its entirety. Single chain antibodies comprise the variable regions of the light and heavy chains joined by a flexible linker moiety. Yet smaller is the antibody fragment known as the single domain antibody, which comprises an isolate VH single domain. Techniques for obtaining a single domain antibody with at least some of the binding specificity of the intact antibody from which they are derived are known in the art. For instance, Ward, et al. in "Binding Activities of a Repertoire of Single Immunoglobulin Variable Domains Secreted from *Escherichia coli*," Nature 341: 644-646, disclose a method for screening to obtain an antibody heavy chain variable region (H single domain antibody) with sufficient affinity for its target epitope to bind thereto in isolate form.

The invention also provides isolated nucleic acids encoding the humanized or chimeric anti-CD99 antibodies, vectors and host cells comprising the nucleic acid, and recombinant techniques for the production of the antibody. Nucleic acids of interest may be at least about 80% identical to the provided nucleic acid sequences, at least about 85%, at least about 90%, at least about 95%, at least about 99%, or identical. In some embodiments a contiguous nucleotide sequence as set forth in any one of SEQ ID NO:1-5 of at least about 20 nt., at least about 25 nt, at least about 50 nt., at least about 75 nt, at least about 100 nt, and up to the complete provided sequence may be used. Such contiguous sequences may encode any or all of the provided CDR sequences, or may encode a complete variable region. As is known in the art, a variable region sequence may be fused to any appropriate constant region sequence.

For recombinant production of the antibody, the nucleic acid encoding it is inserted into a replicable vector for further cloning (amplification of the DNA) or for expression. DNA encoding the monoclonal antibody is readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence.

The anti-CD99 antibody of this invention may be produced recombinantly not only directly, but also as a fusion polypeptide with a heterologous or homologous polypeptide, which include a signal sequence or other polypeptide having a specific cleavage site at the N-terminus of the mature protein or polypeptide, an immunoglobulin constant region sequence, and the like. A heterologous signal sequence selected preferably may be one that is recognized and processed (i.e., cleaved by a signal peptidase) by the host cell. For prokaryotic host cells that do not recognize and process the native antibody signal sequence, the signal sequence is substituted by a prokaryotic signal sequence selected.

An "isolated" nucleic acid molecule is a nucleic acid molecule that is identified and separated from at least one contaminant nucleic acid molecule with which it is ordinarily associated in the natural source of the antibody nucleic acid. An isolated nucleic acid molecule is other than in the form or setting in which it is found in nature. Isolated nucleic acid molecules therefore are distinguished from the nucleic acid molecule as it exists in natural cells. However, an isolated nucleic acid molecule includes a nucleic acid molecule contained in cells that ordinarily express the antibody where, for example, the nucleic acid molecule is in a chromosomal location different from that of natural cells.

Suitable host cells for cloning or expressing the DNA are the prokaryote, yeast, or higher eukaryote cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR(CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1.982)); MRC 5 cells; FS4 cells; and a human hepatoma line (Hep G2). Host cells are transformed with the above-described expression or cloning vectors for anti-CD99 antibody production and cultured in conventional nutrient media modified as appropriate for inducing promoters, selecting transformants, or amplifying the genes encoding the desired sequences.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl) benzene allow for faster flow rates and shorter processing times than can be achieved with agarose. Where the antibody comprises a $CH_3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Methods of Use

The invention further provides methods for reducing growth of cancer cells. The methods provide for decreasing the number of cancer cells expressing CD99, including without limitation lung cancer cells and AML cells. In general, the methods comprise contacting a cancer cell with an antibody provided herein, usually contacting in vivo under conditions that cause cell death of the CD99 expressing cancer cells, e.g. by ADCC, by increase of phagocytosis, etc.

In an embodiment, the cancer is a hematological cancer. In an embodiment, the hematological cancer is a leukemia. In another embodiment, the hematological cancer is a myeloma. In an embodiment, the hematological cancer is a lymphoma.

In an embodiment, the leukemia is selected from acute myeloid leukemia (AML), acute lymphocytic leukemia (ALL), chronic lymphocytic leukemia (CLL) and chronic myelogenous leukemia (CML). In an embodiment, the leukemia is AML. In an embodiment, the leukemia is ALL. In an embodiment, the leukemia is CLL. In a further embodiment, the leukemia is CML. In an embodiment, the cancer cell is a leukemic cell, for example, but not limited to, an AML cell, an ALL cell, a CLL cell or a CML cell.

In other embodiments the cancer is a lung cancer, e.g. SCLC, non-SCLC, particularly SCLC.

"Reducing growth of cancer cells" includes, but is not limited to, reducing proliferation of cancer cells, and reducing the incidence of a non-cancerous cell becoming a cancerous cell. Whether a reduction in cancer cell growth has been achieved can be readily determined using any known assay, including, but not limited to, [$^3$H]-thymidine incorporation; counting cell number over a period of time; detecting and/or measuring CD99, etc.

The present invention provides methods for treating cancer, generally comprising administering to an individual in need thereof an anti-CD99 antibody of the invention, in an amount sufficient to reduce cancer cell growth and treat the cancer. Whether a substance, or a specific amount of the substance, is effective in treating cancer can be assessed using any of a variety of known diagnostic assays for cancer, including, but not limited to biopsy, contrast radiographic studies, CAT scan, and detection of a tumor marker associated with cancer in the blood or biopsy of the individual. The antibody can be administered systemically or locally, usually systemically.

A substance, e.g. a chemotherapeutic drug that reduces cancer cell growth, can be targeted to a cancer cell with an antibody of the invention. Thus, in some embodiments, the invention provides a method of delivering a drug to a cancer cell, comprising administering a drug-antibody complex to a subject, wherein the antibody is specific for CD99, and the drug is one that reduces cancer cell growth, a variety of which are known in the art. Targeting can be accomplished by coupling (e.g., linking, directly or via a linker molecule, either covalently or non-covalently, so as to form a drug-antibody complex) a drug to an antibody specific for a cancer-associated polypeptide. Methods of coupling a drug to an antibody are well known in the art and need not be elaborated upon herein.

Cancers can be staged by analysis of the presence of cancer stem cells. Staging is useful for prognosis and treatment. In one embodiment of the invention, a sample from an cancer patient is stained with an antibody of the invention. In one embodiment, the patient sample is compared to a control, or a standard test value. In another embodiment, the patient sample is compared to a pre-leukemia sample, or to one or more time points through the course of the disease.

Samples, including tissue sections, slides, etc. suspected of containing cancer cells, are stained with reagents specific for CD99, in addition to other cancer specific markers. Samples may be frozen, embedded, present in a tissue microarray, and the like. The reagents, e.g. antibodies, polynucleotide probes, etc. may be detectably labeled, or may be indirectly labeled in the staining procedure. The data provided herein demonstrate that the number and distribution of progenitor cells is diagnostic of the stage of the cancer.

The information thus derived is useful in prognosis and diagnosis, including susceptibility to acceleration of disease, status of a diseased state and response to changes in the environment, such as the passage of time, treatment with drugs or other modalities. The cells can also be classified as to their ability to respond to therapeutic agents and treatments, isolated for research purposes, screened for gene expression, and the like. The clinical samples can be further characterized by genetic analysis, proteomics, cell surface staining, or other means, in order to determine the presence of markers that are useful in classification. For example, genetic abnormalities can be causative of disease susceptibility or drug responsiveness, or can be linked to such phenotypes.

In addition, detection of CD99 positive cells can be used to monitor response to therapy and to aid in prognosis. Clinical samples for use in the methods of the invention may be obtained from a variety of sources, particularly blood, although in some instances samples such as bone marrow, lymph, cerebrospinal fluid, synovial fluid, and the like may be used. Such samples can be separated by centrifugation, elutriation, density gradient separation, apheresis, affinity selection, panning, FACS, centrifugation with Hypaque, etc. prior to analysis, and usually a mononuclear fraction (PBMC) will be used. Once a sample is obtained, it can be used directly, frozen, or maintained in appropriate culture medium for short periods of time. Various media can be employed to maintain cells. The samples may be obtained by any convenient procedure, such as the drawing of blood, venipuncture, biopsy, or the like. Usually a sample will comprise at least about $10^2$ cells, more usually at least about $10^3$ cells, and preferable $10^4$, $10^5$ or more cells. Typically the samples will be from human patients, although animal models may find use, e.g. equine, bovine, porcine, canine, feline, rodent, e.g. mice, rats, hamster, primate, etc.

An appropriate solution may be used for dispersion or suspension of the cell sample. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

Analysis of the cell staining will use conventional methods. Techniques providing accurate enumeration include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide).

The affinity reagents may be specific receptors or ligands for the cell surface molecules indicated above. In addition to antibody reagents, peptide-MHC antigen and T cell receptor pairs may be used; peptide ligands and receptors; effector and receptor molecules, and the like. Antibodies and T cell receptors may be monoclonal or polyclonal, and may be produced by transgenic animals, immunized animals, immortalized human or animal B-cells, cells transfected with DNA vectors encoding the antibody or T cell receptor, etc. The details of the preparation of antibodies and their suitability for use as specific binding members are well-known to those skilled in the art.

Of interest is the use of antibodies as affinity reagents. Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium that maintains the viability of the cells. A preferred medium is phosphate buffered saline containing from 0.1 to 0.5% BSA. Various media are commercially available and may be used according to the nature of the cells, including Dulbecco's Modified Eagle Medium (dMEM), Hank's Basic Salt Solution (HBSS), Dulbecco's phosphate buffered saline (dPBS), RPMI, Iscove's medium, PBS with 5 mM EDTA, etc., frequently supplemented with fetal calf serum, BSA, HSA, etc.

The labeled cells are then quantitated as to the expression of cell surface markers as previously described.

The comparison of a differential analysis obtained from a patient sample, and a reference differential analysis is accomplished by the use of suitable deduction protocols, AI systems, statistical comparisons, etc. A comparison with a reference differential progenitor analysis from normal cells, cells from similarly diseased tissue, and the like, can provide an indication of the disease staging. A database of reference differential progenitor analyses can be compiled. An analysis of particular interest tracks a patient, e.g. in the chronic and pre-leukemic stages of disease, such that acceleration of disease is observed at an early stage. The methods of the invention provide detection of acceleration prior to onset of clinical symptoms, and therefore allow early therapeutic intervention, e.g. initiation of chemotherapy, increase of chemotherapy dose, changing selection of chemotherapeutic drug, and the like.

The humanized or chimeric monoclonal antibodies of the invention can be used in the modulation of phagocytosis in combination with an anti-CD47 reagent, including the methods set forth in International Application US2009/000319, WO 2013/109752 and WO 2011/143624, each herein specifically incorporated by reference in their entirety. For example, antibody compositions of the invention in combination with an anti-CD47 agent may be administered to increase phagocytosis of cancer cells expressing CD99.

An anti-CD47 agent for use in the methods of the invention interferes with binding between CD47 present on a target cell, including without limitation a cancer cell, a cell infected with an intracellular pathogen, a stem cell, etc., to SIRPα present on a phagocytic cell. Generally both such cells are present in the individual being treated. Such methods, in the presence of a pro-phagocytic signal, can increase phagocytosis of the target cell. The subject methods can be used to treat a subject for any disease susceptible to blockade of CD47-mediated SIRPα signaling. Suitable anti-CD47 agents include soluble SIRPα polypeptides; soluble CD47; anti-CD47 antibodies, anti-SIRPα antibodies, and the like, where the term antibodies encompasses antibody fragments and variants thereof, as known in the art.

Typically the dosage of the anti-CD47 agent will be 0.001 to 100 milligrams of protein per kilogram subject body weight. The ratio of anti-CD47 to the anti-CD99 antibody may range from 1:100; 1:50; 1:10; 1:5; 1:2; 1:1; 2:1; 5:1; 10:1; 50:1; 100:1. The agents can be administered to the subject in a series of more than one administration. For therapeutic compositions, regular periodic administration (e.g., every 2-3 days) will sometimes be required, or may be desirable to reduce toxicity. For therapeutic compositions which will be utilized in repeated-dose regimens, antibody moieties which do not provoke HAMA or other immune responses are preferred.

The humanized or chimeric monoclonal antibodies of the invention can be used in vitro and in vivo to monitor the course of CD99 disease therapy. Thus, for example, by measuring the increase or decrease in the number of cells expressing CD99, particularly cancer cells expressing CD99, it can be determined whether a particular therapeutic regimen aimed at ameliorating disease is effective.

The monoclonal antibodies of the invention may be used in vitro in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are flow cytometry, e.g. FACS, MACS, immunohistochemistry, competitive and non-competitive immunoassays in either a direct or indirect format; and the like. Detection of the antigens using the monoclonal antibodies of the invention can be done utilizing immunoassays which are run in either the forward, reverse, or simultaneous modes, including immunohistochemical assays on physiological samples. Those of skill in the art will know, or can readily discern, other immunoassay formats without undue experimentation.

The monoclonal antibodies of the invention can be bound to many different carriers and used to detect the presence of CD99 expressing cells. Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art, which find use as tracers in therapeutic methods, for use in diagnostic methods, and the like. For diagnostic purposes a label may be covalently or non-covalently attached to an antibody of the invention or a fragment thereof, including fragments consisting or comprising of CDR sequences. Examples of the types of labels which can be used in the present invention include enzymes, radioisotopes, fluorescent compounds, colloidal metals, chemiluminescent compounds, and bioluminescent compounds. Those of ordinary skill in the art will know of other suitable labels for binding to the monoclonal antibodies of the invention, or will be able to ascertain such, using routine experimentation. Furthermore, the binding of these labels to the monoclonal antibodies of the invention can be done using standard techniques common to those of ordinary skill in the art.

In some embodiments the antibody or a fragment thereof is attached to a nanoparticle, e.g. for use in imaging. Useful nanoparticles are those known in the art, for example including without limitation, Raman-silica-gold-nanoparticle (R-Si—Au-NP). The R-Si—Au-NPs consist of a Raman organic molecule, with a narrow-band spectral signature, adsorbed onto a gold core. Because the Raman organic molecule can be changed, each nanoparticles can carry its own signature, thereby allowing multiple nanoparticles to be independently detected simultaneously by multiplexing. The entire nanoparticle is encapsulated in a silica shell to hold the Raman organic molecule on the gold nanocore. Optional polyethylene glycol (PEG)-ylation of R-Si—Au-NPs increases their bioavailability and provides functional "handles" for attaching targeting moieties (see Thakor et al (2011) Sci Transl Med. 3(79):79ra33; Jokerst et al. (2011) Small. 7(5):625-33; Gao et al. (2011) Biomaterials. 32(8):2141-8; each herein specifically incorporated by reference).

For purposes of the invention, CD99 may be detected by the monoclonal antibodies of the invention when present in biological fluids and on tissues, in vivo or in vitro. Any sample containing a detectable amount of CD99 can be used. A sample can be a liquid such as urine, saliva, cerebrospinal fluid, blood, serum and the like, or a solid or semi-solid such as tissues, feces, and the like, or, alternatively, a solid tissue such as those commonly used in histological diagnosis.

Another labeling technique which may result in greater sensitivity consists of coupling the antibodies to low molecular weight haptens. These haptens can then be specifically detected by means of a second reaction. For example, it is common to use haptens such as biotin, which reacts with avidin, or dinitrophenol, pyridoxal, or fluorescein, which can react with specific anti-hapten antibodies.

As a matter of convenience, the antibody of the present invention can be provided in a kit, i.e., a packaged combination of reagents in predetermined amounts with instructions for performing the diagnostic assay. Where the antibody is labeled with an enzyme, the kit will include substrates and cofactors required by the enzyme (e.g., a substrate precursor which provides the detectable chromophore or fluorophore). In addition, other additives may be included such as stabilizers, buffers (e.g., a block buffer or lysis buffer) and the like. The relative amounts of the various reagents may be varied widely to provide for concentrations in solution of the reagents which substantially optimize the sensitivity of the assay. Particularly, the reagents may be provided as dry powders, usually lyophilized, including excipients which on dissolution will provide a reagent solution having the appropriate concentration.

Therapeutic formulations comprising one or more antibodies of the invention are prepared for storage by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent the CD99 associated disease.

A pharmaceutical composition may comprise lyophilized antibody, e.g. in a unit formulation of a therapeutic dose; or may be provided as a unit dose in a sterile excipient suitable for administration, e.g. at a concentration of from about 0.01 mg/ml to about 100 mg/ml.

The therapeutic dose may be at least about 0.01 µg/kg body weight, at least about 0.05 µg/kg body weight; at least about 0.1 µg/kg body weight, at least about 0.5 µg/kg body weight, at least about 1 µg/kg body weight, at least about 2.5 µg/kg body weight, at least about 5 µg/kg body weight, and not more than about 100 µg/kg body weight. It will be understood by one of skill in the art that such guidelines will be adjusted for the molecular weight of the active agent, e.g. in the use of antibody fragments, or in the use of antibody conjugates. The dosage may also be varied for localized administration, e.g. intranasal, inhalation, etc., or for systemic administration, e.g. i.m., i.p., i.v., and the like.

The antibody need not be, but is optionally formulated with one or more agents that potentiate activity, or that otherwise increase the therapeutic effect. These are generally used in the same dosages and with administration routes as used hereinbefore or about from 1 to 99% of the heretofore employed dosages.

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules)

or in macroemulsions. Such techniques are disclosed in Remington's Pharmaceutical Sciences 16th edition, Osol, A. Ed. (1980).

The anti-CD99 antibody is administered by any suitable means, including parenteral, subcutaneous, intraperitoneal, intrapulmonary, and intranasal. Parenteral infusions include intramuscular, intravenous, intraarterial, intraperitoneal, or subcutaneous administration. In addition, the anti-CD99 antibody is suitably administered by pulse infusion, particularly with declining doses of the antibody.

For the prevention or treatment of disease, the appropriate dosage of antibody will depend on the type of disease to be treated, as defined above, the severity and course of the disease, whether the antibody is administered for preventive purposes, previous therapy, the patient's clinical history and response to the antibody, and the discretion of the attending physician. The antibody is suitably administered to the patient at one time or over a series of treatments.

In another embodiment of the invention, an article of manufacture containing materials useful for the treatment of the disorders described above is provided. The article of manufacture comprises a container and a label. Suitable containers include, for example, bottles, vials, syringes, and test tubes. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). The active agent in the composition is the anti-CD99 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, syringes, and package inserts with instructions for use.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Humanized and Chimeric Mouse Anti-Human CD99 Monoclonal Antibodies

An anti-CD99 monoclonal antibody, 12E7, bound human CD99 specifically and inhibited tumor growth in vivo. Chimeric and humanized 12E7 antibodies were then designed and constructed based on the original mouse 12E7 to reduce murine antibody immunogenicity. All 12E7-derived antibodies including mouse 12E7, chimeric 12E7-IgG1, and humanized 12E7-IgG1 induced potent phagocytosis in vitro and eliminated AML cells effectively in xenografts model in vivo. Furthermore, mouse 12E7 synergized with anti-CD47 antibody to eradicate AML in vivo. Our findings suggest that anti-CD99 antibodies we developed, either as single agents or in combination, may be used to target AML.

We detected increased expression of CD99 on acute myeloid leukemia stem cells (AML LSC) compared to normal hematopoietic stem cells (HSC), thus representing an AML LSC marker that can be a target for therapeutic monoclonal antibodies (mAb) in the treatment of patients with de novo, relapsed, or refractory AML. A hybridoma clone 12E7 has been previously generated and found to specifically bind human CD99. Here, we describe the cloning of the variable regions of 12E7 and the generation of chimeric and humanized 12E7 antibodies. We demonstrated that both chimeric and humanized 12E7 exhibit potent efficacy in triggering phagocytosis of AML cells in vitro and eliminating AML cells in vivo. Furthermore, we showed that mouse 12E7 synergized with anti-CD47 antibody in eradicating AML in vivo. These results indicate that our 12E7-based monoclonal antibodies can be used either as single agents or in combination strategies for AML therapy.

Results and Discussions

Generation of Monoclonal Antibody Against Human CD99.

A mouse hybridoma clone, 12E7, was identified to produce a monoclonal antibody with specificity against human CD99. Heavy and light chain variable regions of 12E7 were cloned from the hybridoma using universal antibody primers. Multiple clones of each V gene product were sequenced to monitor PCR-induced errors. The nucleotide sequences of VH and VL of 12E7 were determined, and the deduced amino acid sequences are shown in FIGS. 1A and B, respectively. DNA sequence analysis demonstrated that the heavy chain of 12E7 uses a V segment of the IGHV14 family, and that the light chain belongs to the IGKV1 subgroup.

Humanization of 12E7 Antibody.

In order to select human antibody frameworks (FRs) to be used as templates for CDR-grafting, the mouse 12E7 VL and VH regions were compared with those of human germline sequences. The FRs of mouse 12E7 VL region were found to have the highest homology with IGKV2-29 subgroup, and the FRs of the VH region exhibited the highest homology with human IGHV1-2 subgroup. The FRs from human IGKV2-29 and IGHV1-2 were therefore used as the bases for designing the humanized 12E7. Amino acid positions in the FR regions that differ between 12E7 and IGKV2-29/IGHV1-2 sequences and that may have influence in antigen binding were identified through molecular modeling. Identical residues in the FRs were retained and non-identical residues were either retained or substituted based on the molecular modeling program. Sequence alignments of mouse and humanized VH and VL are shown in FIG. 2.

Characterization of Antigen Binding Activity of Humanized 12E7 Antibody.

Mouse and humanized 12E7 variable regions were then constructed onto a human IgG1 scaffold to make chimeric 12E7-G1 (Ch12E7-G1) and humanized 12E7-G1 (Hu12E7-G1), respectively. Transient transfection was carried out in 293 cells, and the resulting antibodies were purified by Protein A affinity chromatography.

Figure 3B:
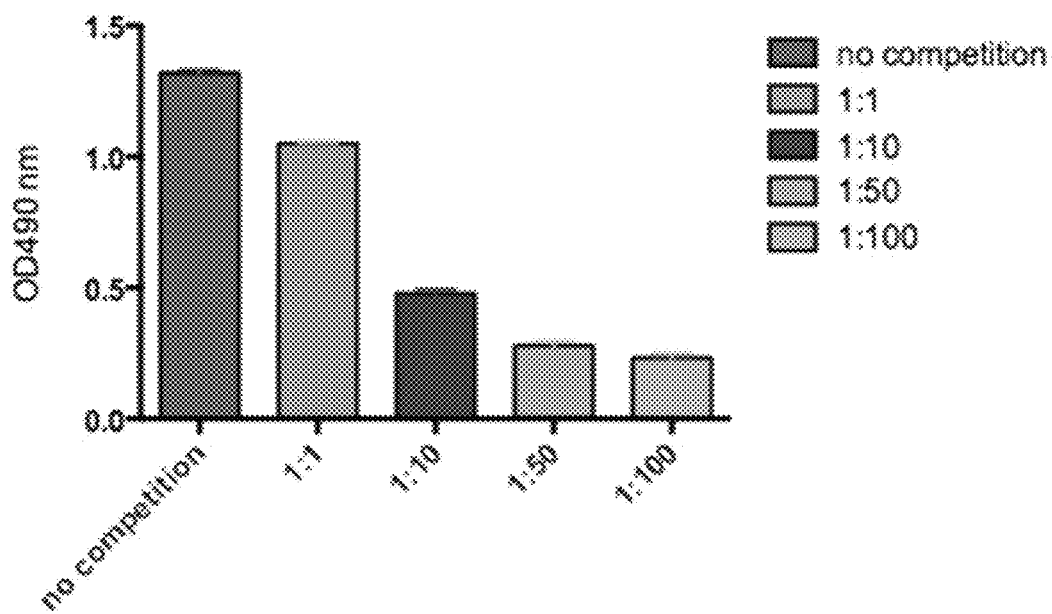

To assess the antigen binding activity of Hu12E7-G1, ELISA was conducted by coating with human CD99/Fc fusion protein as the bait. As shown in FIG. 3A, Hu12E7-G1 bound CD99 in a dose-dependent manner. Moreover, the binding activity of Hu12E7-G1 was comparable to Ch12E7-G1 that possesses the original mouse variable regions of 12E7 antibody, suggesting that Hu12E7-G1 retained similar antigen binding activity as compared to its parental antibody. Furthermore, we conducted competition ELISA between Hu12E7-G1 and the original mouse 12E7. As seen in FIG. 3B, mouse 12E7 bound human CD99. However, its binding activity was reduced when Hu12E7-G1 was added, and the degree of competition coincided with the relative concentration of Hu12E7-G1. These results suggest that Hu12E7-G1 possesses affinity and specificity similar to that of its parental antibody.

Figures 4A, 4B:
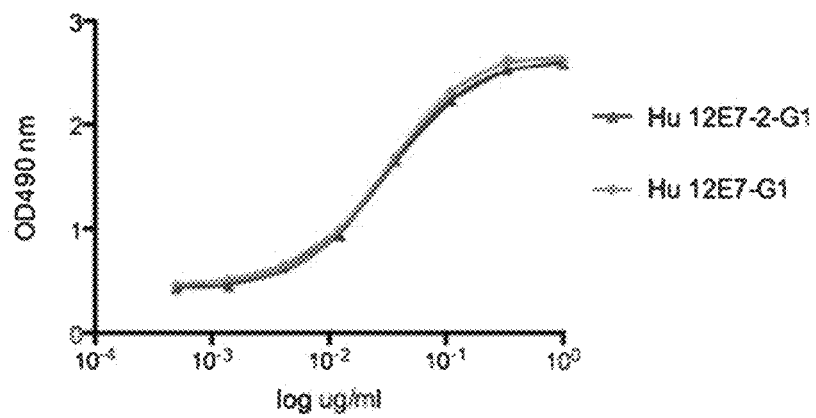
FIG. 4A-4B. Hu12E7-2-G1 with a different framework in the VH region, SEQ ID NO:5, ((FIG. 4A). CDRs are indicated in bold) binds CD99 equivalently to Hu12E7-G1 (FIG. 4BB).

We have also constructed a different version of humanized 12E7-G1 (Hu12E7-2-G1) having a different sequence in the VH region (FIG. 4A), and ELISA binding data showed that it bound CD99 at a comparable level to that of Hu12E7-G1 (FIG. 4B).

Hu12E7-G1 Induces Potent Macrophage-Mediated Phagocytosis of AML.

Figure 5A:
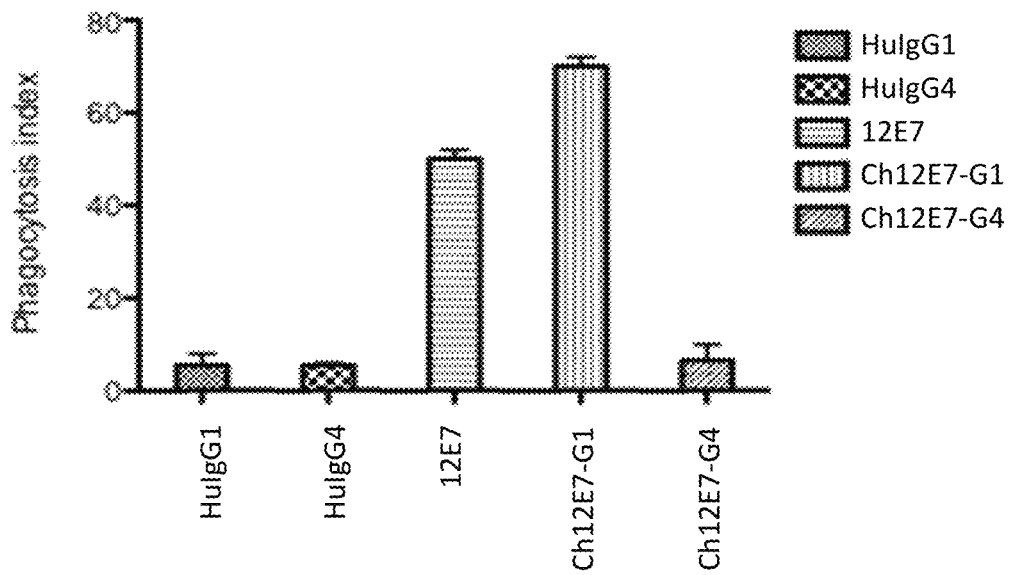
FIG. 5A-5B. Anti-CD99 monoclonal antibodies promote potent phagocytosis of CD99-expressing target cells. HL60-CD99hi (FIG. 5A) and primary human AML cells (FIG. 5B) were labeled with CFSE and incubated with human peripheral blood-derived macrophages in a 4:1 target to effector cell ratio. Two hours later, the macrophages were imaged by fluorescence microscopy to detect phagocytosis. The phagocytic index (number of target cells ingested per 100 macrophages) was determined for each condition in duplicate.

To study the mechanism of action of 12E7 antibodies, we first investigated if 12E7 antibodies elicit phagocytosis that has been demonstrated to play an important role in antibody-mediated antitumor effects. An AML cell line, HL60-CD99hi, was tested in the presence of 12E7 antibodies together with human peripheral blood-derived macrophages. Phagocytic activity was measured by counting the number of ingested CFSE-labeled HL60-CD99$^{hi}$ cells detected by fluorescence microscopy. As seen in FIG. 5A, Ch12E7-G1 efficiently enabled phagocytosis of HL60-CD99hi cells at a level comparable to native mouse 12E7. To determine whether Ch12E7-G1-driven phagocytosis is dependent on the antibody constant (Fc) domain, we constructed Ch12E7-G4 in which mouse 12E7 variable domains were engrafted onto a human IgG4 format. Ch12E7-G4 was unable to stimulate phagocytosis, suggesting the engagement of Fc-receptors is required for Ch12E7-G1-induced phagocytosis.

Figure 5B:
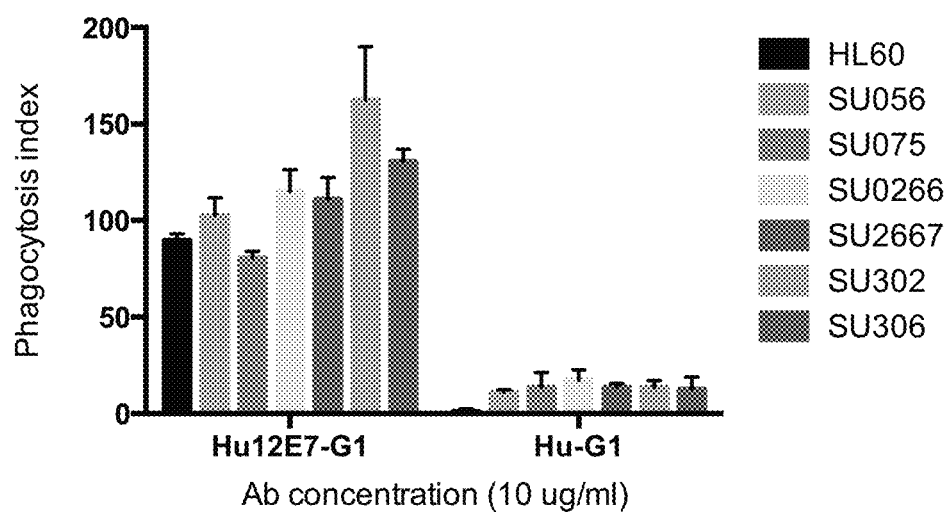

We also tested phagocytosis of primary human AML cells induced by 12E7 antibodies. In this study, Hu12E7-G1 induced potent phagocytosis of six different primary AML samples collected from patients (n=6/6) (FIG. 5B). Taken together, these results indicate that 12E7 antibodies are able to stimulate phagocytosis of CD99-expressing cells by macrophages in an Fc-dependent manner.

Figure 6:
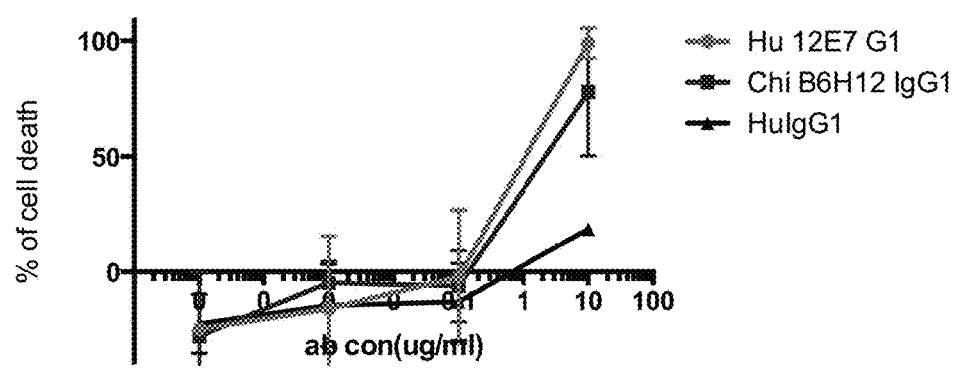
FIG. 6. Hu12E7-G1 potently induces ADCC. Antibody-dependent cellular cytotoxicity (ADCC) was investigated using human peripheral blood mononuclear cells (PBMC) as effectors and HL60-CD99$^{hi}$ as target cells in vitro. An anti-CD47 antibody, Chi B6H12 IgG1 served as a positive control.

Hu12E7-G1 induces antibody-dependent cellular cytotoxicity (ADCC). Antibodies that bind to specific cell-surface antigens on target cells can induce cytotoxicity via antibody-dependent cellular cytotoxicity (ADCC) mediated by the Fc constant region of the antibody, particularly human IgG1 Fc. Since humanized 12E7 was constructed as a human IgG1 format, we next investigated the ability of Hu12E7-G1 to mediate ADCC. An ACELLA-TOX™ Bioluminescence-based cytotoxicity assay was performed, in which HL60-CD99$^{hi}$ cells were used as the target cells and human IL-2-stimulated PBMC were used as the effector cells at an E/T ratio of 100:1. As illustrated in FIG. 6, Hu12E7-G1, but not HuIgG1, effectively induced ADCC in a dose-dependent manner. Consistent with our previous data, chB6H12-G1, which is an antibody specific for human CD47, was able to mediate ADCC, and thus was used as a positive control in this experiment.

In addition, the capacity of Hu12E7-G1 to mediate complement-dependent cytotoxicity (CDC) was assessed with HL60-CD99$^{hi}$ cells. However, no Hu12E7-G1-mediated CDC was observed against HL60-CD99$^{hi}$ cells, although rituximab, which was used as a positive control, was able to trigger CDC against Raji cells. Moreover, induction of apoptosis was evaluated using an Annexin V flow cytometry assay with HL60-CD99$^{hi}$ cells. Hu12E7-G1 did not trigger apoptosis of HL60-CD99$^{hi}$ cells.

Altogether, data shown here indicates that the anti-human CD99 antibody, Hu12E7-G1, is able to induce phagocytosis and mediate ADCC, both in an Fc-dependent manner, against CD99-expressing target cells.

Hu12E7-G1 Eliminates Primary Human AML Cells In Vivo.

Figure 7A:
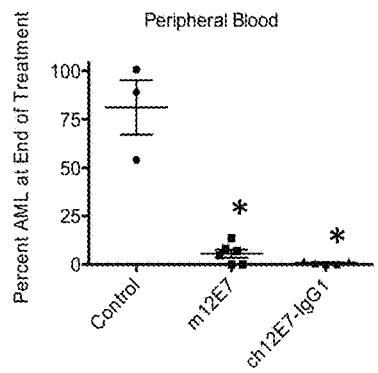
FIG. 7A-7C(i). Anti-Human CD99 Monoclonal Antibodies Eliminate Primary Human AML Cells In Vivo.
Figure 7B:
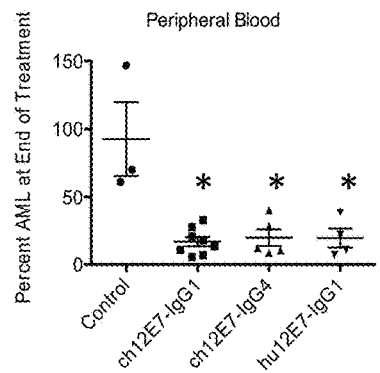
Figure 7A:
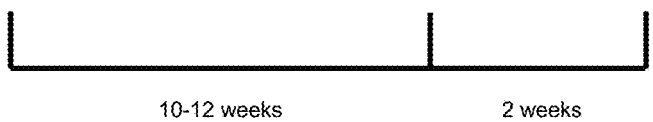

To evaluate the ability of our anti-CD99 antibodies to eliminate primary human AML in vivo, we utilized an established disease model allowing AML cells to engraft robustly in immunodeficient NSG mice prior to starting therapy. A treatment strategy was employed in which mice were administered daily intraperitoneal injections of 100 µg of each of the anti-CD99 antibodies or a control antibody for 2 weeks. At the end of the 14 days, the peripheral blood was reassessed for leukemic engraftment by flow cytometry. Both mouse 12E7 antibody and chimeric 12E7-G1 showed a statistically significant and marked reduction in leukemic engraftment in the peripheral blood compared to control (FIG. 7A). These results further confirmed that the variable regions of 12E7 antibody we cloned from the mouse hybridoma contain the correct VL and VH sequences. In a second xenotransplantation experiment, Hu12E7-G1 was used to treat the mice in parallel with the chimeric 12E7-G1 or chimeric 12E7-G4. At the end of the 14 days, the peripheral blood was reassessed for leukemic engraftment by flow cytometry. All three 12E7-derived antibodies showed a statistically significant and marked reduction in leukemic engraftment in the peripheral blood compared to control (FIG. 7B). These results indicate that Hu12E7-G1 is efficacious in eliminating AML cells in vivo.

Figure 7C:
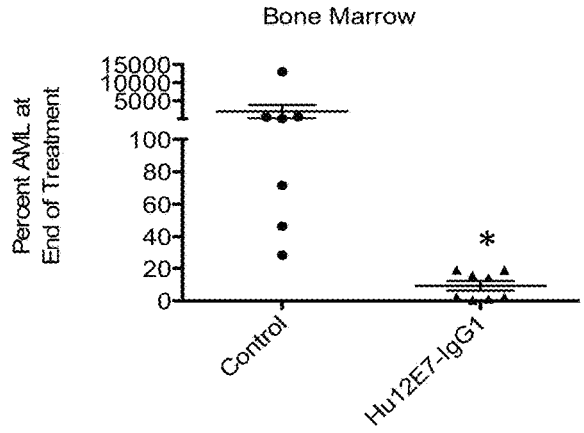
Figure 7C:

To test different primary human AML patient samples for their response to Hu12E7-G1 treatment, we engrafted another two independent primary human AML cells into immunodeficient NSG mice. Ten weeks later, engraftment of AML was assessed in the bone marrow and mice were assigned to treatment with control mouse IgG or Hu12E7-G1 antibody. Mice were treated with 14 days of antibody with daily 200 µg doses. At the end of the 14 days, the bone marrow was reassessed for leukemic engraftment by flow cytometry. Hu12E7-G1 showed a statistically significant and marked reduction in leukemic engraftment in the bone marrow compared to control (FIG. 7C). Therefore, Hu12E7-G1 is effective in eliminating leukemic cells in the peripheral blood and bone marrow for multiple different primary patient samples.

Anti-CD99 Monoclonal Antibody Synergizes with Anti-CD47 Antibody to Eliminate Primary Human AML Cells In Vivo.

Figure 8:
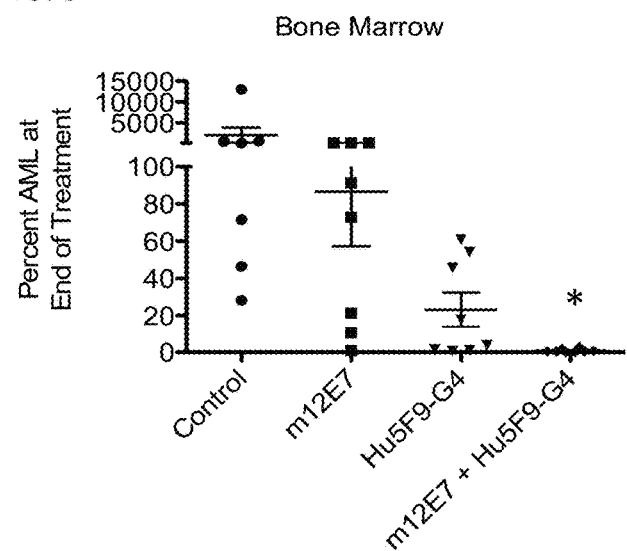
FIG. 8-8(i).
Figure 8I:
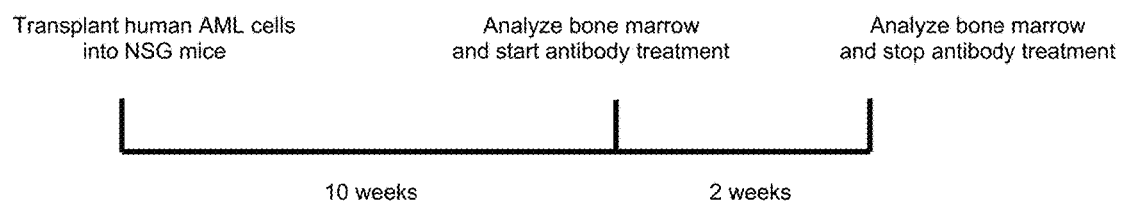

We have previously developed a humanized anti-human CD47 antibody termed Hu5F9-G4. Expression of CD47 and CD99 is increased in AML LSC compared to HSC, and anti-CD47 antibodies potently stimulate the phagocytosis and elimination of AML LSC in vitro and in vivo. Moreover, we showed that anti-CD47 antibodies can synergize with anti-tumor antibodies that efficiently engage Fc receptors. Thus, we tested the effect of 12E7 antibody in combination with Hu5F9-G4 against primary AML in vivo. Primary human AML cells from two independent cases were transplanted into immunodeficient NSG mice. 10 weeks later, engraftment of AML was assessed in the bone marrow and mice were assigned to treatment with control mouse IgG, mouse anti-human CD99 (m12E7) antibody, Hu5F9-G4, or combination of m12E7 and Hu5F9-G4. Mice were treated with 14 days of antibody with daily 200 μg doses of 12E7 or 10 μg doses of Hu5F9-G4. At the end of the 14 days, the bone marrow was reassessed for leukemic engraftment by flow cytometry. Consistent with our previous data, Hu5F9-G4 inhibited tumor growth dramatically even with 10 μg doses. Although m12E7 was less effective in this study, combination treatment with Hu5F9-G4 showed a statistically significant and marked reduction in leukemic engraftment in the bone marrow compared to either antibody alone (FIG. 8).

In summary, our results demonstrate that our 12E7-based anti-CD99 monoclonal antibodies are potent in eliminating AML cells both in vitro and in vivo. Moreover, the anti-CD99 antibody-mediated tumor inhibition effect synergizes with that of anti-CD47 antibody. The results provide the scientific basis for the development of novel CD99-targeted antibody therapies for AML.

Materials and Methods

Antibody V Cloning and Sequencing.

The cloning strategy used here involved an initial RNA isolation from 12E7 hybridoma cells (Qiagen). The cDNA sequences encoding the heavy and light chain variable regions of 12E7 monoclonal antibody were obtained using 5' RACE-PCR techniques (Clontech) and were sequenced using standard DNA sequencing techniques.

Molecular Modeling and Antibody Humanization.

Humanization of mouse anti-CD99 12E7 antibody was performed by installing CDR residues from mouse antibody into human germline framework (FR). Differences between mouse 12E7 and the human FR residues were individually modeled to investigate their possible influence on CDR conformation. Humanized VH and VL genes were synthesized by McLab (South San Francisco, Calif.).

Cell Transfection.

293F cells were cultured under FreeStyle™ 293 Expression Medium (Invitrogen). Transient transfection was performed by co-transfection of expression vectors encoding antibody heavy chain and light chain using 293fectin transfection reagent (Invitrogen), according to the manufacturer's instructions. Four to five days later, supernatants from the transfected cells were harvested and tested for antibody secretion by ELISA. Briefly, 96-well plates (Nunc, Roskilde, Denmark) were coated with 1 μg/ml goat anti-human Fc gamma antibody in phosphate-buffered saline (PBS) for 16 hr at 4° C. After blocking for 1 hr with 0.4% BSA in PBS at room temperature, isolated supernatants were added in ⅓ sequential dilutions, and incubated for 1 hr at room temperature. Plates were subsequently washed three times and incubated with HRP-conjugated goat anti-human kappa-specific antibody for 1 hr at room temperature. After washing, plates were developed with OPT. The reaction was stopped with 2M $H_2SO_4$, and OD was measured at 490 nM.

Antibody Purification and Characterization.

The culture supernatant was applied to protein A SEPHAROSE™ columns. The column was washed with PBS, and protein was then eluted with eluting buffer (0.1 M sodium citrate buffer, pH 3.0). Collected fractions were neutralized with 1 M Tris pH 9.0. Finally, purified samples were dialyzed against PBS. Purity of the eluted antibody fraction was analyzed by sodium dodecyl sulfate polyacrylamide gel electrophoresis (SDS-PAGE) on 10% gels under reducing or non-reducing conditions. Bands were visualized by Coomassie brilliant blue staining.

Phagocytosis Assay.

Fresh buffy coat obtained from the Stanford Blood Center was processed over Ficoll to obtain peripheral blood mononuclear cells (PBMC). $1.5 \times 10^6$ PBMC were plated in 10 ml of IMDM growth medium (IMDM+10% Human AB serum+Glutamax+pen/strep) and incubated at 37 degree for 8 days. At day 8, human macrophages were fully developed and trypsinized. $5 \times 10^4$ cells in 200 μl of IMDM growth medium were added into each well of a 24-well plate for overnight incubation in order for macrophages to attach to the plate. A final concentration of 10 μg/ml of mouse 12E7, Ch12E7-G1, Ch12E7-G4, Hu12E7-G1, or HuIgG1 isotype control was added to 24 well plates containing human macrophages. Target cells (primary AML or HL60-CD99hi) were labeled by CFSE. $2 \times 10^5$ target cells (primary AML or HL60-CD99$^{hi}$) in 100 μl of IMDM growth medium were added to each well, mixed, and incubated at 37° C. for 2 hours (effector:target=1:4). Phagocytosis index was obtained by counting the number of phagocytic target cells per 100 effector cells by fluorescence microscopy.

ADCC Assay.

ADCC was conducted according to the manufacturer's instructions using the ACELLA-TOX™ Bioluminescence Cytotoxicity kit (Cell Technology Inc. Cat# CLATOX100-3). In brief, human PBMC were incubated overnight at $10^6$/ml in IMDM human complete medium with 400 units/ml human IL-2. The next day, activated PBMC were used as effector cells. $5 \times 10^3$ HL60-CD99$^{hi}$ cells in 25 μl IMDM human complete medium were added per well in an U-bottom 96 well plate, and 25 μl IMDM human complete medium containing different antibodies at the indicated concentrations was added to each well. After 5 min incubation at 37° C., $2.5 \times 10^5$ PBMC in 25 μl IMDM human complete medium were added to each well to give an effector:target (E/T) cell ratio of 100:1. Then, the mixtures were incubated at 37° C. for another 4 hours, followed by detection with the kit reagents.

In Vivo Antibody Treatment of Human AML Engrafted Mice.

About $1 \times 10^6$ primary AML cells were transplanted intravenously into adult NSG mice. Ten to twelve weeks later, engraftment of AML was assessed in the bone marrow and peripheral blood. Mice were then treated with the indicated antibodies for 14 days. At the end of the 14 days, the bone marrow and peripheral blood were reassessed for leukemic engraftment by flow cytometry and the treatment was stopped.

What is claimed is:

1. An isolated humanized antibody that specifically binds to human CD99, and comprises a heavy chain variable region comprising each of the CDR sequences set forth in SEQ ID NO:6-8 and a light chain variable region comprising each of the CDR sequences set forth in SEQ ID NO:9-11.

2. The humanized antibody of claim 1, wherein said the light chain variable region comprises the amino acid sequence set forth in SEQ ID NO:4.

3. The humanized antibody of claim 1, wherein said the heavy chain variable region comprises the amino acid sequence set forth in SEQ ID NO:2 or 5.

4. A polynucleotide encoding an antibody set forth in claim 1.

5. An isolated cell that produces an antibody set forth in claim 1.

6. A pharmaceutical composition comprising an antibody set forth in claim 1 and a pharmaceutically acceptable excipient.

7. A method of treating a human CD99-expressing cancer in a subject, the method comprising the step of administering to a subject having said CD99-expressing cancer a therapeutically effective amount of an antibody set forth in claim 1 in a dose effective to reduce the number of cancer cells in the subject, wherein the antibody comprises an Fc region and is capable of mediating ADCC directed against the CD99-expressing cancer cells in the subject and/or Fc-dependent macrophage-mediated phagocytosis of the CD99-expressing cancer cells in the subject and/or wherein the antibody is coupled to a chemotherapeutic drug.

8. A method of treating a human subject for a CD99-expressing cancer, the method comprising:
   administering to the subject an effective dose of (i) an antibody as set forth in claim 1 wherein the antibody comprises an Fc region and is capable of mediating ADCC directed against the CD99-expressing cancer cells in the subject and/or Fc-dependent macrophage-mediated phagocytosis of the CD99-expressing cancer cells in the subject; and (ii) at least one additional therapeutic agent.

9. The method of claim 7, wherein the cancer is acute myelogenous leukemia (AML).

10. The method of claim 8, wherein the cancer is acute myelogenous leukemia (AML).

11. The method of claim 8, wherein the at least one additional therapeutic agent is a chemotherapeutic drug.

* * * * *

SEQUENCE LISTING

<160> NUMBER OF SEQ ID NOS: 11

<210> SEQ ID NO 1
<211> LENGTH: 114
<212> TYPE: PRT
<213> ORGANISM: Mus musculus

<400> SEQUENCE: 1

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Arg Arg Pro Glu Gln Gly Leu Glu Trp Ile
        35                  40                  45

Gly Arg Ile Asp Pro Ala Asn Gly Asn Thr Lys Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Arg Gly Gly Val Asp Trp Gly Gln Gly Thr Leu Val Thr Val
            100                 105                 110

Ser Ala

<210> SEQ ID NO 2
<211> LENGTH: 114
<212> TYPE: PRT
<213> ORGANISM: Artificial sequence
<220> FEATURE:
<223> OTHER INFORMATION: synthetic amino acid sequence

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Lys Asp Thr
            20                  25                  30

Tyr Ile His Trp Val Arg Gln Ala Pro Gly Gln Gly Leu Glu Trp Met
        35                  40                  45

Gly Arg Ile Asp Pro Ala Asn Gly Asn Thr Lys Tyr Asp Pro Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Arg Gly Gly Val Asp Trp Gly Gln Gly Thr Leu Val Thr Val
            100                 105                 110

Ser Ser

<210> SEQ ID NO 3
<211> LENGTH: 112
<212> TYPE: PRT
<213> ORGANISM: Mus musculus

<400> SEQUENCE: 3

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Gly
            20                  25                  30

```
Asp Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
 50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Leu Gly Val Tyr Tyr Cys Trp Gln Gly
                 85                  90                  95

Thr His Phe Pro Arg Thr Phe Gly Gly Gly Thr Lys Leu Glu Ile Lys
            100                 105                 110

<210> SEQ ID NO 4
<211> LENGTH: 112
<212> TYPE: PRT
<213> ORGANISM: Artificial sequence
<220> FEATURE:
<223> OTHER INFORMATION: synthetic amino acid sequence

<400> SEQUENCE: 4

Asp Ile Val Met Thr Gln Thr Pro Leu Ser Leu Ser Val Thr Pro Gly
 1               5                  10                  15

Gln Pro Ala Ser Ile Ser Cys Lys Ser Ser Gln Ser Leu Leu Asp Gly
                 20                  25                  30

Asp Gly Lys Thr Tyr Leu Asn Trp Leu Leu Gln Lys Pro Gly Gln Ser
            35                  40                  45

Pro Gln Arg Leu Ile Tyr Leu Val Ser Lys Leu Asp Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Trp Gln Gly
                 85                  90                  95

Thr His Phe Pro Arg Thr Phe Gly Gln Gly Thr Lys Leu Glu Ile Lys
            100                 105                 110

<210> SEQ ID NO 5
<211> LENGTH: 114
<212> TYPE: PRT
<213> ORGANISM: Artificial sequence
<220> FEATURE:
<223> OTHER INFORMATION: synthetic amino acid sequence

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Phe Asn Ile Lys Asp Thr
                 20                  25                  30

Tyr Ile His Trp Val Arg Gln Ala Pro Gly Gln Gly Leu Glu Trp Met
            35                  40                  45

Gly Arg Ile Asp Pro Ala Asn Gly Asn Thr Lys Tyr Asp Pro Lys Phe
 50                  55                  60

Gln Gly Arg Val Thr Met Thr Arg Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Ala Arg Arg Gly Gly Val Asp Trp Gly Gln Gly Thr Leu Val Thr Val
            100                 105                 110

Ser Ser
```

```
<210> SEQ ID NO 6
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 6

Asp Thr Tyr Ile His
1               5

<210> SEQ ID NO 7
<211> LENGTH: 17
<212> TYPE: PRT
<213> ORGANISM: Artificial sequence
<220> FEATURE:
<223> OTHER INFORMATION: synthetic amino acid sequence

<400> SEQUENCE: 7

Arg Ile Asp Pro Ala Asn Gly Asn Thr Lys Tyr Asp Pro Lys Phe Gln
1               5                   10                  15

Gly

<210> SEQ ID NO 8
<211> LENGTH: 5
<212> TYPE: PRT
<213> ORGANISM: Artificial sequence
<220> FEATURE:
<223> OTHER INFORMATION: synthetic amino acid sequence

<400> SEQUENCE: 8

Arg Gly Gly Val Asp
1               5

<210> SEQ ID NO 9
<211> LENGTH: 16
<212> TYPE: PRT
<213> ORGANISM: Artificial sequence
<220> FEATURE:
<223> OTHER INFORMATION: synthetic amino acid sequence

<400> SEQUENCE: 9

Lys Ser Ser Gln Ser Leu Leu Asp Gly Asp Gly Lys Thr Tyr Leu Asn
1               5                   10                  15

<210> SEQ ID NO 10
<211> LENGTH: 7
<212> TYPE: PRT
<213> ORGANISM: Artificial sequence
<220> FEATURE:
<223> OTHER INFORMATION: synthetic amino acid sequence

<400> SEQUENCE: 10

Leu Val Ser Lys Leu Asp Ser
1               5

<210> SEQ ID NO 11
<211> LENGTH: 9
<212> TYPE: PRT
<213> ORGANISM: Artificial sequence
<220> FEATURE:
<223> OTHER INFORMATION: synthetic amino acid sequence
```

```
<400> SEQUENCE: 11

Trp Gln Gly Thr His Phe Pro Arg Thr
1               5
```